US010191545B1

(12) United States Patent
Laszlo et al.

(10) Patent No.: US 10,191,545 B1
(45) Date of Patent: Jan. 29, 2019

(54) CONTENT PRESENTATION (71) Applicant: X Development LLC, Mountain View, CA (US)

(72) Inventors: Sarah Ann Laszlo, Binghamton, NY (US); Gabriella Levine, San Francisco, CA (US); Philip Edwin Watson, Santa Cruz, CA (US); Matthew Dixon Eisaman, Port Jefferson, NY (US); Brian John Adolf, San Mateo, CA (US)

(73) Assignee: X Development LLC, Mountain View, CA (US)

(*) Notice: Subject to any disclaimer, the term of this patent is extended or adjusted under 35 U.S.C. 154(b) by 43 days.

(21) Appl. No.: 15/391,038

(22) Filed: Dec. 27, 2016

(51) Int. Cl.
*A61B 5/04* (2006.01)
*G06F 3/01* (2006.01)
*G06T 11/60* (2006.01)

(52) U.S. Cl.
CPC .............. *G06F 3/015* (2013.01); *G06T 11/60* (2013.01); *G06T 2200/24* (2013.01)

(58) Field of Classification Search
CPC ...... G06F 3/015; G06T 11/60; G06T 2200/24
See application file for complete search history.

(56) References Cited

U.S. PATENT DOCUMENTS

| 9,269,027 | B1 | 2/2016 | Khosla et al. | |
|---|---|---|---|---|
| 2002/0197589 | A1* | 12/2002 | Wood | G09B 19/02 434/201 |
| 2013/0260361 | A1* | 10/2013 | Mutlu | G09B 19/00 434/365 |
| 2015/0351655 | A1* | 12/2015 | Coleman | A61B 5/0482 600/301 |
| 2017/0337834 | A1* | 11/2017 | Shindi | G09B 5/02 |

OTHER PUBLICATIONS

Mathewson, K. E., et al. "To See or Not to See: Prestimulus α Phase Predicts Visual Awareness." Journal of Neuroscience 29.9 (2009): 2725-732.

Mathewson, Kyle E., et al. "Making Waves in the Stream of Consciousness: Entraining Oscillations in EEG Alpha and Fluctuations in Visual Awareness with Rhythmic Visual Stimulation." Journal of Cognitive Neuroscience 24.12 (2012): 2321-333.

Skelly, Jun. J. et al., "Attentional Pacing and Temporal Capture in Slow Visual Sequences." United States Air Force Research Laboratory, Sep. 2000, Interim Report for the period Apr. 1999 to Sep. 2000, 50 pages, AFRL-HE-WP-TR-2003-0078.

* cited by examiner

*Primary Examiner* — Ibrahim A Khan
(74) *Attorney, Agent, or Firm* — Fish & Richardson P.C.

(57) ABSTRACT

Methods, systems, and apparatus, including computer programs encoded on a computer storage medium, for receiving brain activity data of a user from a brain wave sensor. Identifying Alpha wave activity from the brain activity data. Determining a synchronization timing for presenting content to the user such that the content appears on a display device during a predetermined phase of the Alpha wave activity based on the Alpha wave activity. Causing the content to be displayed on the display device according to the synchronization timing, where the content includes a first content item and a second content item that is associated with the first content item.

20 Claims, 4 Drawing Sheets

CONTENT PRESENTATION

TECHNICAL FIELD

This disclosure generally relates to synchronizing the presentation of data to a user based on measurements of the user's brain waves.

BACKGROUND

Research has shown that Alpha brain waves (typically measured between 10 and 12 Hz in adult humans)) can act as an inhibitor to detecting visual stimuli. For example, the effects of Alpha brain waves on stimulus recognition are discussed in the articles Mathewson, K. E., et al. "To See or Not to See: Prestimulus α Phase Predicts Visual Awareness." *Journal of Neuroscience* 29.9 (2009): 2725-732 and Mathewson, Kyle E., et al, "Making Waves in the Stream of Consciousness: Entraining Oscillations in EEG Alpha and Fluctuations in Visual Awareness with Rhythmic Visual Stimulation." *Journal of Cognitive Neuroscience* 24.12 (2012): 2321-333, both of which are hereby incorporated herein by reference. That is, a person's ability to detect (e.g., notice) a visual stimulus such as an image on a display is improved during particular phases of an Alpha wave.

SUMMARY

The specification describes systems, methods, devices, and other techniques to improve the ability of users to process content presented to them based on the user's brain waves. Particular phases of an Alpha wave have been shown affect a person's ability to detect (e.g., notice) a visual stimulus such as an image on a display. In a sense, the Alpha waves can be thought of as acting as a gating function for sensory perception in the brain; allowing sensory data in during wave troughs and blocking sensory data during peaks. Implementations disclosed herein harness this understanding to provide computer systems or computer controlled content presentation systems (e.g., visual displays and audio systems) that present content to a user in a manner that improves the user's ability to perceive and retain the presented content. For example, a user's ability to learn may be improved by presenting content from computer-based educational or training curricula in synchronization with the user's Alpha brain wave pattern. The user may more readily perceive the content presented, and therefore, be more apt to process, understand, and, later, recall the information conveyed by the content.

Towards that end, the ideas described herein generally relate to a system that receives a brain wave data from a user and synchronizes the timing for presenting content to the based on the user's brain wave data. For example, the system can include a wearable brainwave monitor in secure communication with a computing device (e.g., a laptop computer, desktop computer, smartphone, tablet computer, virtual reality headset, etc.) executing educational software. The software can monitor the user's Alpha wave pattern and synchronize the presentation of content by the computing device such that the content is presented during the appropriate phase of the user's Alpha wave pattern for effective learning.

The software may include a calibration process, in which the display timing is calibrated to adjust for latencies in the system. The calibration process can be used to synchronize the system processing such that the content actually appears on the display during the appropriate phase of the user's Alpha wave while accounting for such latencies.

In general, innovative aspects of the subject matter described in this specification can be embodied in methods that include the actions of receiving brain activity data of a user from a brain wave sensor. Identifying Alpha wave activity from the brain activity data. Determining a synchronization timing for presenting content to the user such that the content appears on a display device during a predetermined phase of the Alpha wave activity based on the Alpha wave activity. Causing the content to be displayed on the display device according to the synchronization timing, where the content includes a first content item and a second content item that is associated with the first content item. Other implementations of this aspect include corresponding systems, apparatus, and computer programs, configured to perform the actions of the methods, encoded on computer storage devices. These and other implementations can each optionally include one or more of the following features.

In some implementations, the first content item explains the second content item. Some implementations include receiving, in response to displaying the content, a user input indicating an association made by the user based on the content displayed to the user in response to displaying the content, and determining, based on the user input, whether the user has made a correct association based on the content displayed to the user. Some implementations include presenting an output, to the user, that indicates whether the user made the correct association with the content.

In some implementations, determining a synchronization timing for presenting content to the user such that the content appears on a display device during a predetermined phase of the user's Alpha wave activity includes determining a delay associated with presentation of content on the display, where the synchronization timing accounts for the delay.

In some implementations, determining whether the user has made a correct association based on the content displayed to the user includes determining that the user has made an incorrect association based on the content displayed to the user. Some implementations include causing the content to be redisplayed on the display device according to the synchronization timing.

In some implementations, determining whether the user has made a correct association based on the content displayed to the user includes determining that the user has made a correct association based on the content displayed to the user. Some implementations include causing new content to be displayed on the display device according to the synchronization timing.

Some implementations include presenting, to the user after having displayed the content, a question related to the content, where the user input indicating an association made by the user based on the content displayed to the user is an answer to the question.

In some implementations, the content includes visual content and audio content. In some implementations, the brain wave sensor is part of a brain wave sensor system and the brain activity data is received from the brain wave sensor system.

In another general aspect, the subject matter described in this specification can be embodied in methods that include the actions of receiving brain activity data of a user from a brain wave sensor. Identifying Alpha wave activity from the brain activity data. Determining a synchronization timing for presenting content to the user such that the content appears on a display device during a predetermined phase of the Alpha wave activity based on the Alpha wave activity. Causing the content to be displayed on the display device according to the synchronization timing. Receiving, in response to displaying the content, a user input indicating an association made by the user based on the content displayed to the user. Determining, based on the user input, whether the user has made a correct association based on the content displayed to the user. Presenting an output, to the user, that indicates whether the user made the correct association with the content. Other implementations of this aspect include corresponding systems, apparatus, and computer programs, configured to perform the actions of the methods, encoded on computer storage devices.

Particular implementations of the subject matter described in this specification can be implemented so as to realize one or more of the following advantages. Implementations of the present disclosure may improve the operation of computer controlled displays, audio systems, or both so as to present content to a user in synchronization with the user's natural perception patterns. Implementations may enable a user to learn vocabulary of a new language faster. Implementations may teach a user to make discriminations between types of objects (e.g., between cancerous and noncancerous images in radiography scans, between weapons and non-weapons in baggage screening images) more accurately and rapidly. Implementations may teach a user to partially or fully overcome certain learning disabilities, such as dyslexia. Implementations may teach a user to learn a specific skill (e.g., as engine repair) faster. Implementations may teach a user to learn braille faster.

The details of one or more implementations of the subject matter of this disclosure are set forth in the accompanying drawings and the description below. Other features, aspects, and advantages of the subject matter will become apparent from the description, the drawings, and the claims.

DESCRIPTION OF DRAWINGS

Like reference numbers and designations in the various drawings indicate like elements.

DETAILED DESCRIPTION

Figure 1:
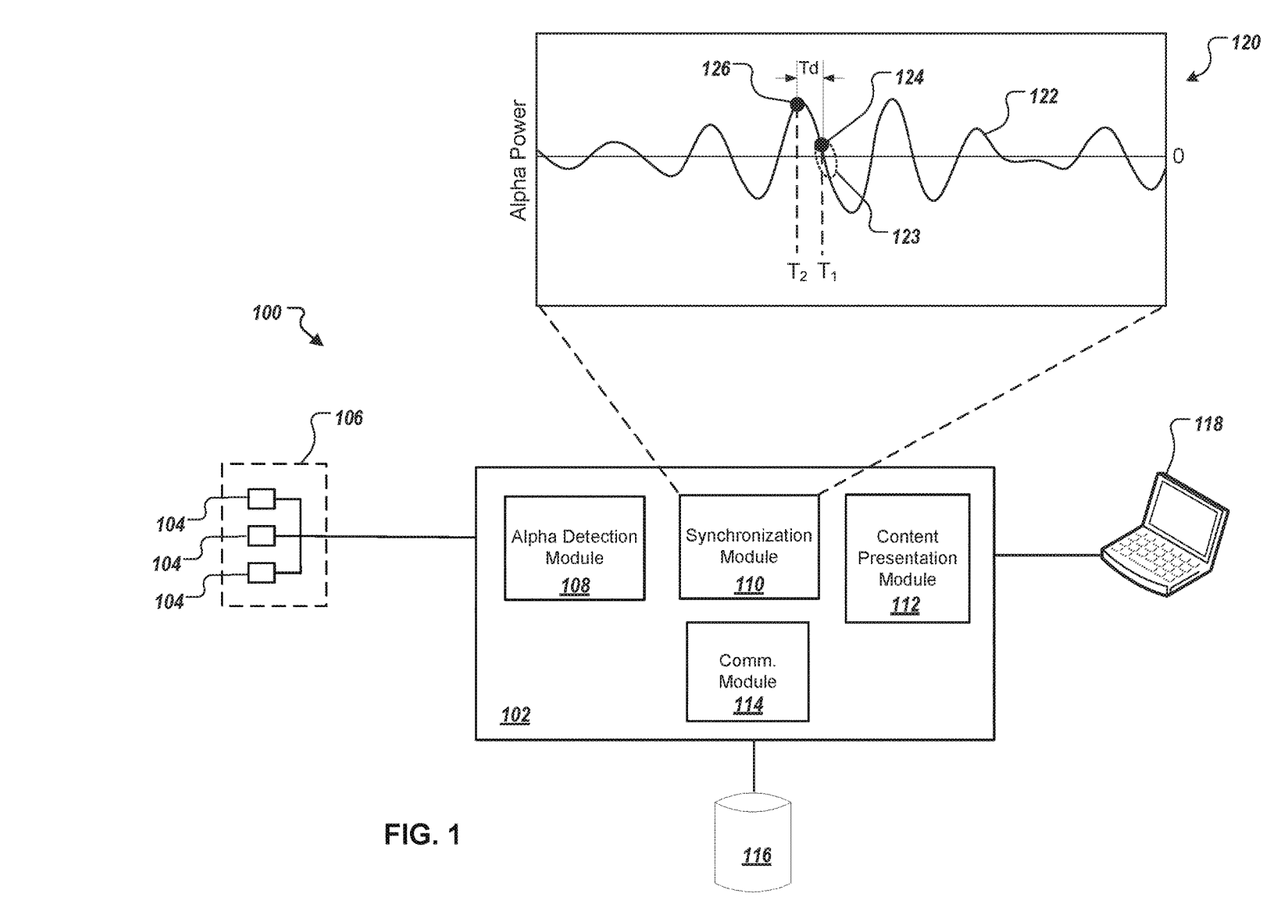
FIG. 1 depicts block diagram of an example system for synchronizing content presentation with a user's brain waves in accordance with implementations of the present disclosure.

FIG. 1 depicts a block diagram of an example system 100 for synchronizing the presentation of content with a user's brain waves. The system includes a data processing module 102 which is in communication with brain wave sensors 104. The data processing module 102 can be implemented as a hardware or a software module. For example, the data processing module can be a hardware or software module that is incorporated into a computing system such as a brain wave monitoring system, a desktop or laptop computer, a mobile device (e.g., a tablet computer or smartphone) or a wearable device (e.g., a virtual reality headset). The data processing module 102 includes several sub-modules which are described in more detail below. As a whole, the data processing module 102 receives user brain-wave data from the brain wave sensors 104. The data processing module 102 identifies Alpha waves in the brain wave data and synchronizes the presentation of audio/visual content with the Alpha waves of the user.

For example, users may more readily perceive and process information that is presented during a particular phase of their Alpha brain wave cycle. More particularly, a user's vigilance is improved during the lower power portion of the Alpha wave cycle which places the user in a heightened state for perceiving and retaining information. However, this state changes rapidly, e.g., lasting less than about 40 ms for a typical 12 Hz Alpha cycle. To leverage the user's heightened vigilance during this state, the data processing module 102 synchronizes the presentation of content to the user such that the content is presented during the low power portion of the user's Alpha wave cycle.

The presented content can include audio content, graphical or video content, tactile content, or a combination thereof. For example, an educational curriculum such as a language training program may use Alpha synchronization to audibly present new vocabulary words along with their definition to a user during the user's heightened state of vigilance. As another example, an aviation or seamanship navigation training program may use Alpha synchronization to graphically present new visual recognition data such as landmarks or navigation aids along with their meanings to a user during the user's heightened state of vigilance. As another example, a pre-school educational curriculum may use may use Alpha synchronization to present images of numbers and letters along and audible names of the letters and numbers during a child's heightened state of vigilance to teach preschoolers the Alphabet and numbers.

The data processing module 102 can also verify a user's retention of the presented content. The data processing module 102 may present several content items before verifying a user's retention of one or more of the content items. For example, the data processing module 102 can present the user with one or more questions related to one of the presented content items. Based on the user's response to the question, the data processing module 102 can determine whether the user made a correct association based on the content item. If the association is correct, the user has likely retained data represented by the content.

In general, any sensors capable of detecting brain waves may be used. For example, the brain wave sensors 104 can be one or more individual electrodes (e.g., multiple EEG electrodes) that are connected to the data processing module 102 by wired connection. The brain wave sensors 104 can be part of a brain wave sensor system 106 that is in communication with the data processing module 102. A brain wave sensor system 106 can include multiple individual brain wave sensors 104 and computer hardware (e.g., processors and memory) to receive, process, and/or display data received from the brain wave sensors 104. Example brain wave sensor systems 106 can include, but are not limited to, EEG systems, a wearable brain wave detection device (e.g., as described below in reference to FIG. 2 below), a magnetoencephalography (MEG) system, and an Event-Related Optical Signal (EROS) system, sometimes also referred to as "Fast NIRS" (Near Infrared spectroscopy). A brain wave sensor system 106 can transmit brain wave data to the data processing module 102 through a wired or wireless connection.

Figure 2:
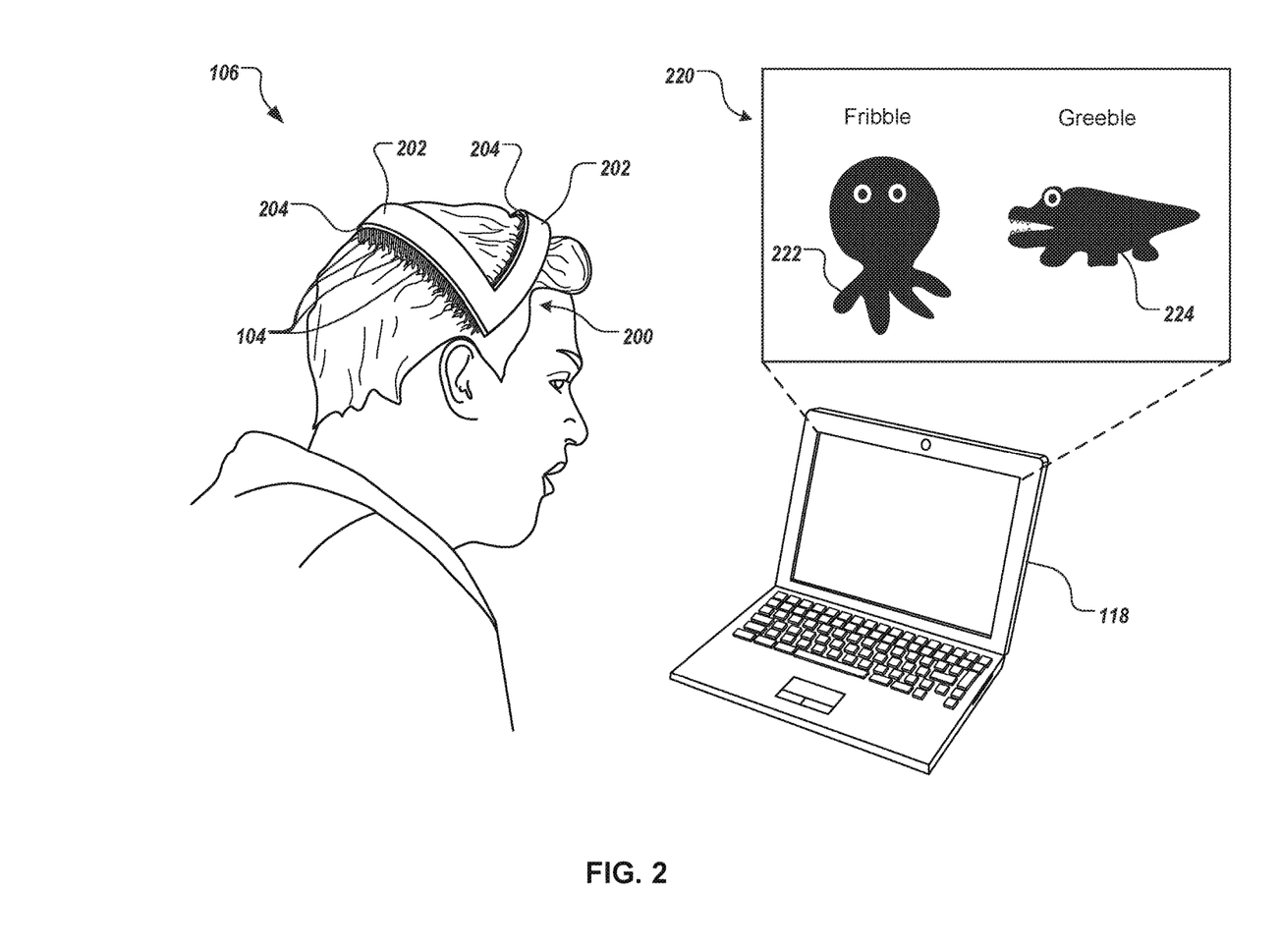
FIG. 2 depicts an example brain wave sensor system according to implementations of the present disclosure.

FIG. 2 depicts an example brain wave sensor system 106. The sensor system 106 is a wearable device 200 which includes a pair of bands 202 that fit over a user's head. Specifically, the wearable device 200 includes one band which fits over the front of a user's head and the other band 202 which fits over the back of a user's head, securing the device 200 sufficiently to the user during operation. The bands 202 include a plurality of brain-wave sensors 104. The sensors 104 can be, for example, electrodes configured to sense the user's brain waves through the skin. For example, the electrodes can be non-invasive and configured to contact the user's scalp and sense the user's brain waves through the scalp. In some implementations, the electrodes can be secured to the user's scalp by an adhesive.

The sensors 104 are distributed across the rear side 204 of each band 202. In some examples, the sensors 104 can be distributed across the bands 202 in to form a comb-like structure. For example, the sensors 104 can be narrow pins distributed across the bands 202 such that a user can slide the bands 202 over their head allowing the sensors 104 to slide through the user's hair, like a comb, and contact the user's scalp. Furthermore, the comb-like structure sensors 104 distributed on the bands 202 may enable the device 200 to be retained in place on the user's head by the user's hair. In some implementations, the sensors 104 are retractable. For example, the sensors 104 can be retracted into the body of the bands 202.

In some implementations, the wearable device 200 can be a virtual reality headset that includes brainwave sensors. In some implementations, the wearable device 200 can be a bone conduction headset that includes brainwave sensors. In some implementations, the wearable device 200 can be a garment (e.g., a hat or headband) that includes brainwave sensors.

The wearable device 200 is in communication with a computing device 118, e.g., a laptop, tablet computer, desktop computer, smartphone, or brain wave data processing system. For example, the data processing module 102 can be implemented as a software application on a computing device 118. The wearable device 200 communicates brain wave data received from the sensors 104 to the computing device 118. In some implementations, the data processing module 102 can be implemented as a hardware or software module on the wearable device 200. In such implementations, the device 200 can communicate content or content synchronization timing to the computing device 118 for use by other applications on the computing device, e.g., educational or skills training application.

Referring again to FIG. 1, the data processing module 102 includes several sub-modules, each of which can be implemented in hardware or software. The data processing module 102 includes an Alpha detection module 108, a synchronization module 110, a content presentation module 112, and a communication module 114. The data processing module 102 can be implemented as a software application executed by computing device 118. The data processing module 102 is in communication with a data store 116. The data store 116 stores audio and/or graphical content for presentation to a user. The data store 116 can be local to the data processing module. The data store 116 can be remoted from the data processing module and accessed through one or more computer networks.

The communication module 114 provides a communication interface for the data processing module 102 with the brain wave sensors 104. The communication module 114 can be a wired communication (e.g.; USB, Ethernet, fiber optic), wireless communication module (e.g.; Bluetooth, ZigBee, WiFi, infrared (IR)). The communication module 114 can serve as an interface with other computing devices 118, e.g.; computing devices that may be used to present content to a user. The communication module 114 can be used to communicate directly or indirectly, e.g., through a network, with other remote computing devices 118 such as, e.g., a laptop, a tablet computer, a smartphone, a virtual reality headset, etc.

The Alpha detection module 108 receives an electrical signal representing brain waves of the user from the brain wave sensors 104. The Alpha detection module 108 detects Alpha brain wave patterns within signals. For example, the electrical signal may represent a combination of different brain wave patterns from the individual. That is, a brain wave sensor 104 can detect electromagnetic signals emanating from a user's brain which include signal patterns related to multiple different types of brain waves (e.g.; Alpha brain waves, Gamma brain waves, Beta brain waves, Delta brain waves, and Theta brain waves). The different types of brain wave patterns can be distinguished based on differentiating characteristics between the different brain wave types, e.g.; frequency, waveshape, sensor location (e.g., alpha is typically largest over the back of the head can be distinguished from other wave sources based on which sensor(s) a particular wave pattern is received from). For example, the Alpha detection module 108 may detect Alpha brain wave patterns by filtering the signal from a brain wave sensor 104. For example, an Alpha pattern may be detected by filtering the signal from a brain wave sensor 104 with a band pass filter centered around the characteristic frequency of an Alpha signal (e.g., between 10-12 Hz in neurologically normal adults).

In some implementations, the Alpha detection module 108 can use matched filters to detect and extract Alpha wave patterns, canonical artifact waveshapes to extract signal pattern which correlate with known stereotyped Alpha waveshapes, band pass filters to remove spectral effects of the identified signal pattern, or a combination thereof.

In some implementations, the alpha detection module 108 includes filters such as a low pass filter, high pass filter, band pass filter, or a combination thereof. For example, a low pass filter can be tuned to remove stationary power artifacts from the received signals. For example, the low pass filter can be tuned to filter out signals to above approximately 30 Hz to remove stationary power artifacts such as 60 Hz signals in US power systems and 50 Hz signals in European power systems. As another example, a high pass filter may be tuned to filter out signals below approximately 0.2 Hz to remove drift artifacts from, for example, sweating.

In some implementations, the alpha detection module 108 can perform complex signal removal processes such as spatial unmixing techniques (e.g., Independent Component Analysis), neural network techniques (e.g., de-noising auto encoders), or a combination thereof. For example, the alpha detection module 108 can use Independent Components Analysis to remove signals related to a user's blinks identifying and removing or reducing any signal patterns in the EEG signal that are temporally correlated with a canonical (e.g., stereotyped) blink signal.

In some implementations, the Alpha detection module 108 may perform an Alpha wave training process to identify a more precise Alpha frequency for a given user. For example, Alpha wave frequencies can vary from person to person. Thus, the Alpha detection module 108 can incorporate a training process in which it identifies the frequency of a given user's Alpha wave activity.

In some implementations, the alpha detection module 108 includes an amplifier to amplify detected alpha waves.

The Alpha detection module 108 can pass the detected Alpha wave signals to the synchronization module 110. The synchronization module 110 determines synchronization timing for presenting content from the data store 116 to a user such that the content is presented to the user during a predetermined phase of the user's Alpha wave activity. For example, the synchronization module 110 synchronizes the presentation of content to a user such that the content is presented to the user during at least a portion of the lower power phase of the user's Alpha brain activity. Graph 120 illustrates an example Alpha brain wave pattern 122 of a user. The synchronization module 110 can determine a synchronization timing for presenting content to the user such that the content is initially presented at time $T_1$. As shown, time $T_1$ corresponds to the beginning of the lower power phase (region 123) of the user's Alpha activity. Thus, the content would be presented to the user during a majority of the lower power phase. For example, graphical content can be displayed at time $T_1$ and can be retained on a display screen for the entirety of the lower Alpha phase or for several cycles of the user's Alpha activity. In other words, once the content is presented in phase with the user's Alpha activity, the content may be continuously presented to the user for any duration of time (e.g., for one Alpha cycle, multiple Alpha cycles, several seconds, several minutes, or until a user provides an input to remove or change the content).

The synchronization module 110 can synchronize the timing for presenting content with the user's Alpha activity by determining a trigger point 124 based on the Alpha activity. For example, the trigger point may be an amplitude or power value of the Alpha activity pattern 122 that indicates the onset of the predetermined phase (e.g., the low power portion of the Alpha wave). For example, as shown in graph 120 the power or amplitude of the Alpha activity pattern at point 124 may be the trigger value for causing the content to be presented to the user. The synchronization module 110 can use Alpha power peaks to trigger synchronization timing. For example, when the frequency of a user's Alpha wave is detected by the Alpha detection module 108 and passed to the synchronization module 110, the synchronization module can determine a period of time to wait for the low power phase after a power peak occurs. For example, the low power phase occurs a quarter wave cycle after a power peak, for a 12 Hz Alpha wave frequency the synchronization module 110 can delay the synchronization timing for 83 ms after the power peak.

The synchronization module 110 can account for system delays in presenting content. That is, system 100 may require some non-negligible processing time from triggering the presentation of the content to the user and when the content is actually presented. The synchronization module 110 can determine a synchronization timing that accounts for a system delay time ($T_d$) between when the presentation of content is initiated by the system 100 and when the content is actually presented to a user. Based on the user's Alpha activity, the synchronization module 110 can determine an appropriate phase shift in the synchronization timing such that the content is actually presented to the user during the desired portion of the user's Alpha activity while taking into account the system delay timing ($T_d$). For example, the synchronization module 110 can shift the synchronization timing to trigger the presentation of the content at time $T_2$, e.g., at trigger point 126, the peak of the user's Alpha activity. Based on the system delay time ($T_d$) the content will then actually be presented to the user at time which corresponds to the desired phase of the user's Alpha activity.

In some implementations, the delay timing ($T_d$) may be a known value for a given system 100. In such implementations, the synchronization module 110 can analyze a given user's Alpha activity and determine an appropriate synchronization timing based on the given user's Alpha activity to account for the system's delay timing. For example, the synchronization module 110 can determine a nominal frequency of the user's Alpha wave activity. The synchronization module 110 can convert the known delay time of the system into a phase value relative the frequency of the user's Alpha wave activity. For example, a delay time of 1 ms can be converted to a phase shift of approximately 4 degrees for a 12 Hz Alpha wave pattern. The synchronization module 110 can then trigger the presentation of desired content when the user's Alpha activity reaches a trigger value that occurs 4 degrees prior to the predetermined phase at which the presentation of the content is desired (e.g., 4 degrees before point 124).

If the synchronization module 110 detects that the user's Alpha activity has changed after a period of time, the synchronization module 110 can recalculate the synchronization timing. For example, if the frequency of the user's Alpha activity changes to 11.5 Hz, the synchronization module 110 can recalculate the phase shift of the synchronization timing. Similarly, if the average power of the user's Alpha activity changes, the synchronization module 110 can recalculate trigger values for triggering the presentation of the content.

The content presentation module 112 coordinates the presentation of content (e.g., educational or training content) to a user according to the synchronization timing established by the synchronization module 110. For example, the content presentation module 112 can obtain content for presentation to the user from the data store 116. The content presentation module 112 controls a computing device 118 to present the content to a user in synchronization with the user's Alpha wave activity pattern. The content presentation module 112 can control an audio system of the computing device 118 to present audio content in synchronization with the user's Alpha wave activity pattern. The content presentation module 112 can control a display of the computing device 118 to present graphical or video content in synchronization with the user's Alpha wave activity pattern. The content presentation module 112 can control both an audio system and a display of the computing device 118 to present a combination of graphical and audio content in synchronization with the user's Alpha wave activity pattern.

The content presented by the content presentation module 112 can include two or more content items that have an association between them. Moreover, the content items presented may be chosen in order for the user to learn the association between them. For example, the content items can include a new vocabulary word and its definition. In such an example, the user may be expected to learn the definition of the word.

The content presentation module 112 can verify the user's retention of the presented content. For example, the content presentation module 112 can receive a user input in response to the presented content. The content presentation module 112 may present the user with a question related to the content and a set of user selectable answers to the question. The user's response will indicate whether the user recalls the content and whether the user made a correct association based on the content presented to the user. If the user answers the question correctly, the user has likely retained the presented content correctly (or at least a portion of the content). This feedback can be used to optimize parameters such as frequency and delay timing.

Referring to FIGS. 1 and 2; to take a simplistic example for purposes of illustration, a user may be learning about two fictitious animals; a fribble and a greeble. The content presentation module 112 can cause the computing device 118 to present an image 220 to the user that illustrates a fribble 222 and a greeble 224. The image 220 is presented in synchronization with the user's Alpha activity pattern. The image 220 may include a label identifying each animal to the user. In addition; the content presentation module 112 may cause the audio system of the computing device to play audio announcing the names of the animals to the user. Although illustrated as both animals being presented to the user in one image; the animals may be presented to the user separately in two different images; one showing the fribble 222 and one showing the greeble 224, with a respective label. Yet; each image will be presented in synchronization with the user's alpha wave activity pattern.

In order to verify the user's understanding and retention of the presented content, the content presentation module 112 can subsequently present the users with a series of questions about the fribble and greeble. For example; the questions can be obtained from the data store 116. The questions can be quiz questions associated with an educational or training curriculum (e.g., a zoology curriculum related to exotic animals). For example, the content presentation module 112 can present an image of one of the animals without a label and ask the user to identify the animal. Other questions might include: "How many tentacles does a fribble have?"; "Which animal is most likely a carnivore?"; and "Which animal is more reptilian?" The user's answers to such questions will be demonstrative of whether the user made correct associations with the presented content; and thus, whether the user has correctly understood and retained the presented content. The content presentation module 112 can determine whether the user's responses to the questions are correct and whether to represent the same content to the user for review or to proceed to presenting new content. The content presentation module 112 provides feedback indicating whether the user's answers to the questions were correct. In some implementations, the content presentation module 112 does not present feedback to the user after the user answers a question. In some implementations, the content presentation module 112 selectively presents feedback to the user after the user answers a question. For example, the content presentation module 112 may only present feedback when the user's answer is incorrect, or only when the user's answer is correct.

For example, the content presentation module 112 can continue to represent the mages of the fribble 222 and greeble 224 in synchronization with the user's Alpha wave activity and provide questions about the fribble and greeble until the content presentation module 112 determines that the user has adequately retained a desired portion of the presented content. For example, when the user correctly answers a threshold number of questions about the fribble 222 and greeble 224 (e.g., 80%), then the content presentation module 112 may proceed to present new content. For example, the content presentation module can present information about the fribble and greeble's habitats or present information about different animals.

In some implementations, the content presentation module 112 may present a series of different content before quizzing the user on the presented content. For example, the content presentation module can present a series of labeled images of multiple animals in a fictitious zoology curriculum, with each image being presented in synchronization with the user's Alpha activity, before presenting any questions about the animals in order to gauge the user's understanding and retention.

While the simplistic example of the fribble and greeble has been used to illustrate the operation of system 100, system 100 can be used to aid a user in learning content from a wide variety of educational or training curricula including, but not limited to, vocabulary (e.g., grade school vocabulary, standardized test preparation vocabulary, foreign language vocabulary), foreign language learning (e.g., grammar, vocabulary, pronunciation, etc.), memorization (e.g., for speeches or acting), and pattern detection. For example, system 100 can present content from a language training program. The system 100 can present new vocabulary words along with their translation to a user during the user's heightened state of vigilance to improve the user's vocabulary memorization. As another example, system 100 can present content for memorization to a user. The system 100 can present lines for a play or lines from a user's speech to the user during the user's heightened state of vigilance.

Figure 3:
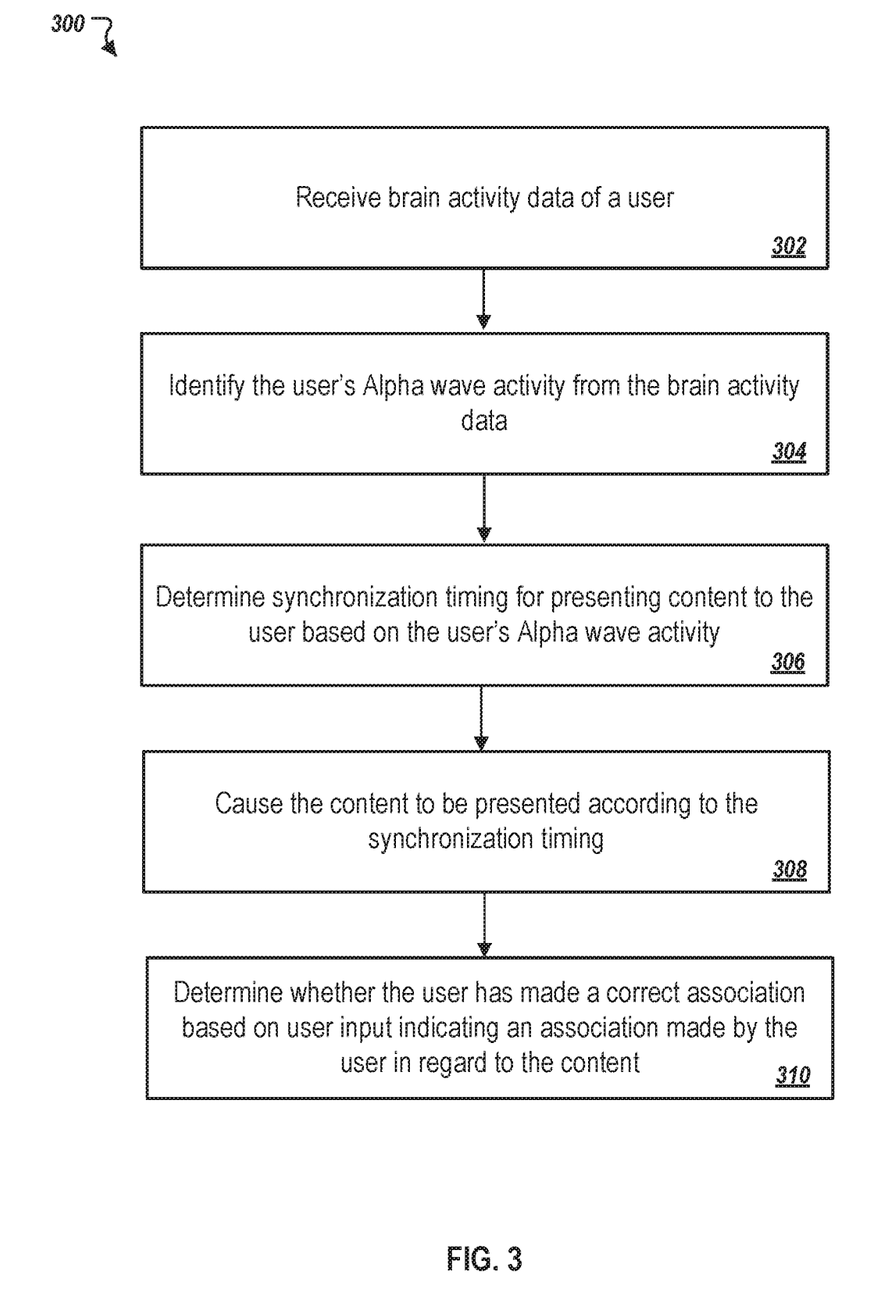
FIG. 3 depicts a flowchart of an example process for synchronizing content presentation with a user's brain waves in accordance with implementations of the present disclosure.

FIG. 3 depicts a flowchart of an example process for synchronizing content presentation with a user's brain waves. In some implementations, the process 300 can be provided as one or more computer-executable programs executed using one or more computing devices. In some examples, the process 300 is executed by a system such data as processing module 102 of FIG. 1, or a computing device such as computing device 118 or wearable device 200 of FIGS. 1 and 2.

The system receives brain activity data of a user from brain wave sensors and user physiological data from non-brain wave sensors (302). The brain activity data includes signal patterns representing one or more types of brain waves of the user (e.g., Alpha brain waves, Gamma brain waves, Beta brain waves, Delta brain waves, and Theta brain waves).

The system identifies the user's Alpha wave activity from within the brain activity data (304). For example, the system distinguishes the Alpha wave pattern from amongst other brain wave patterns in the brain activity data. The system can filter out the non-Alpha brain wave patterns. For example, the system can use matched filters to detect and extract Alpha wave patterns, canonical artifact waveshapes to extract signal pattern which correlate with known stereotyped Alpha waveshapes, band pass filters to remove spectral effects of the identified signal pattern, or a combination thereof.

The system determines synchronization timing for presenting content to the user based on the user's Alpha wave activity (306). The system analyzes the Alpha brain activity pattern to determine a synchronization timing for presenting content to the user. The synchronization timing is determined so that the content is presented to the user during the at least a portion of a predetermine phase of the user's Alpha wave pattern such as the lower power phase of the user's Alpha brain wave pattern. The system can identify an power level of the user's Alpha wave activity to act as a trigger point for initiating the presentation of the content. The trigger point can also be associated with an instantaneous slope of the Alpha wave pattern. In some implementations, the synchronization timing accounts for processing delays within the system such that the presentation of the content is initiated a sufficient time period before the user's Alpha activity reaches the predetermined phase, thereby, causing the content to be present to the user at the predetermined phase.

The system causes the content to be presented according to the synchronization timing (308). For example, when the user's Alpha activity reaches or passes the trigger point, the system initiates the presentation of one or more content items. The content can include audio content, graphical or video content, or both. For example, the content can include content associated with an educational or training curriculum. The content can include two or more content items that are associated to each other. For example, one of the content items can explain the second content item. For example, the content can include content items such as a word along with its definition. As another example, one content item may be presented visually, such as a symbol, and a second content item presented audibly, such as the meaning of the symbol (e.g., an image of a traffic sign and an explanation of the traffic sign's meaning).

The system can present a series of different content items; each being presented in synchronization with the user's Alpha activity. For example, a first image may be presented to the user for a fixed interval of time (e.g., a period of seconds or minutes). After the interval of time has elapsed, the system can present a second image to the user. However, the system may not present the new image precisely at the expiration of the interval of time. For example, after the time interval expires the system can delay the presentation of the second image to ensure that the second image is presented in synchronization with the user's Alpha activity. The system can wait to present the second image until the user's Alpha activity meets or passes the trigger point.

In some implementations, a new content item can be presented upon receiving a user input. For example, the first image (e.g., a slide in a slide show) may be retained on a display until the user provides an input (e.g., a mouse clicks or voice command) to present the second image (e.g., a subsequent slide). However, the system may not immediately present the second image in response to the user input. The system may delay presenting the second image to synchronize the presentation of the image with the user's Alpha activity. For example, after the system receives the user input, the system can wait to present the second image until the user's Alpha activity meets or passes the trigger point. Although data presentation can be delayed in response to a user input, such delays are less than about 50 ms and will likely be unnoticeable by a user.

The system determines whether the user has made a correct association based on user input indicating an association made by the user in regard to the content (310). For example, the system can provide the user with one or more questions to verify the user's understanding and retention of the presented content. The system can receive a user input in response to the questions. The user's response to the question will indicate whether the user recalls the content and whether the user made a correct association based on the content presented to the user. If the user answers the question correctly, the user has likely retained the presented content correctly (or at least a portion of the content). For example, based on the user input responding to the question, the system can determine whether the user has made a correct association based on the content (e.g., whether the user has correctly answered the question). If the user input indicates an incorrect answer, the system can represent the same content to the user in synchronization with the user's Alpha activity. If the user input indicates a correct answer, the system can present different content to the user in synchronization with the user's Alpha activity. In some implementations, the system may represent content to the user if the user answers a threshold number of questions incorrectly.

Figure 4:
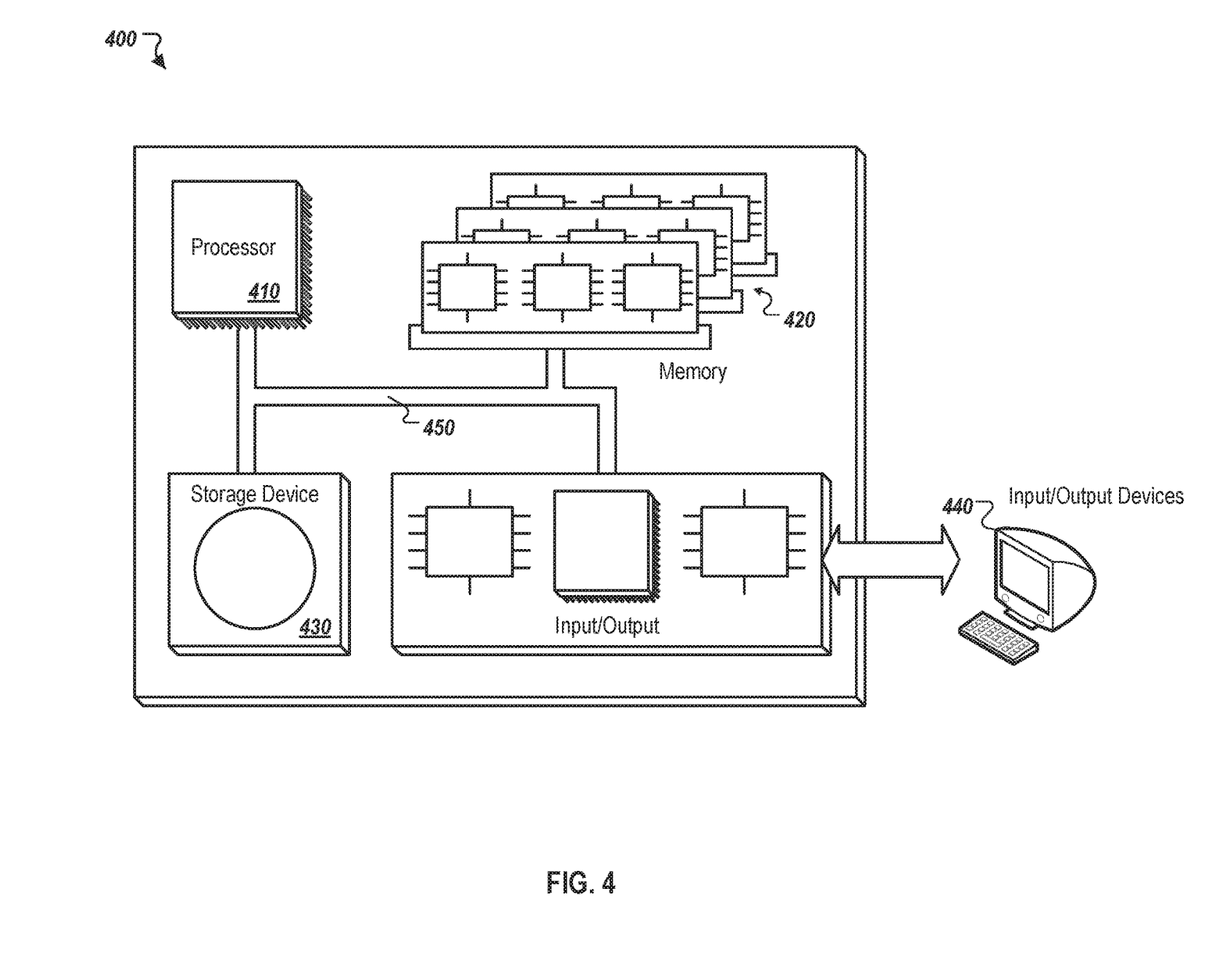
FIG. 4 depicts a schematic diagram of a computer system that may be applied to any of the computer-implemented methods and other techniques described herein.

FIG. 4 is a schematic diagram of a computer system 400. The system 400 can be used to carry out the operations described in association with any of the computer-implemented methods described previously, according to some implementations. In some implementations, computing systems and devices and the functional operations described in this specification can be implemented in digital electronic circuitry, in tangibly-embodied computer software or firmware, in computer hardware, including the structures disclosed in this specification (e.g., system 400) and their structural equivalents, or in combinations of one or more of them. The system 400 is intended to include various forms of digital computers, such as laptops, desktops, workstations, personal digital assistants, servers, blade servers, mainframes, and other appropriate computers, including vehicles installed on base units or pod units of modular vehicles. The system 400 can also include mobile devices, such as personal digital assistants, cellular telephones, smartphones, and other similar computing devices. Additionally, the system can include portable storage media, such as, Universal Serial Bus (USB) flash drives. For example, the USB flash drives may store operating systems and other applications. The USB flash drives can include input/output components, such as a wireless transducer or USB connector that may be inserted into a USB port of another computing device.

The system 400 includes a processor 410, a memory 420, a storage device 430, and an input/output device 440. Each of the components 410, 420, 430, and 440 are interconnected using a system bus 450. The processor 410 is capable of processing instructions for execution within the system 400. The processor may be designed using any of a number of architectures. For example, the processor 410 may be a CISC (Complex Instruction Set Computers) processor, a RISC (Reduced Instruction Set Computer) processor, or a MISC (Minimal Instruction Set Computer) processor.

In one implementation, the processor 410 is a single-threaded processor. In another implementation, the processor 410 is a multi-threaded processor. The processor 410 is capable of processing instructions stored in the memory 420 or on the storage device 430 to display graphical information for a user interface on the input/output device 440.

The memory 420 stores information within the system 400. In one implementation, the memory 420 is a computer-readable medium. In one implementation, the memory 420 is a volatile memory unit. In another implementation, the memory 420 is a non-volatile memory unit.

The storage device 430 is capable of providing mass storage for the system 400. In one implementation, the storage device 430 is a computer-readable medium. In various different implementations, the storage device 430 may be a floppy disk device, a hard disk device, an optical disk device, or a tape device.

The input/output device 440 provides input/output operations for the system 400. In one implementation, the input/output device 440 includes a keyboard and/or pointing device. In another implementation, the input/output device 440 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer. Additionally, such activities can be implemented via touchscreen flat-panel displays and other appropriate mechanisms.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products. Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A computer-implemented method executed by one or more processors and comprising:

receiving brain activity data of a user from a brain wave sensor;

identifying Alpha wave activity from the brain activity data;

determining, based on the Alpha wave activity, a synchronization timing for presenting content to the user such that the content appears on a display device during a predetermined phase of the Alpha wave activity, the synchronization timing including a trigger point of the user's Alpha wave activity that indicates an onset of the predetermined phase;

determining a processing delay between triggering presentation of content and presenting the content on the display, wherein the synchronization timing accounts for the delay; and in response to detecting the trigger point of the user's Alpha wave activity, causing the content to be displayed on the display device according to the synchronization timing, the content including a first content item and a second content item that is associated with the first content item.

2. The method of claim 1, wherein the predetermined phase of the Alpha wave activity is a low power portion of the Alpha wave activity.

3. The method of claim 1, further comprising:
receiving, in response to displaying the content, a user input indicating an association made by the user based on the content displayed to the user; and
determining, based on the user input, whether the user has made a correct association based on the content displayed to the user.

4. The method of claim 3, further comprising presenting, to the user, an output that indicates whether the user made the correct association with the content.

5. The method of claim 3, further comprising presenting, to the user after having displayed the content, a question related to the content, wherein the user input indicating an association made by the user based on the content displayed to the user is an answer to the question.

6. The method of claim 1, wherein determining whether the user has made a correct association based on the content displayed to the user comprises determining that the user has made an incorrect association based on the content displayed to the user, the method further comprising causing the content to be redisplayed on the display device according to the synchronization timing.

7. The method of claim 1, wherein determining whether the user has made a correct association based on the content displayed to the user comprises determining that the user has made a correct association based on the content displayed to the user, the method further comprising causing new content to be displayed on the display device according to the synchronization timing.

8. The method of claim 1, wherein the content includes visual content and audio content.

9. The method of claim 1, wherein the brain wave sensor is part of a brain wave sensor system and the brain activity data is received from the brain wave sensor system.

10. A system comprising:
a brain wave sensor; and
a computing system communicably coupled to the brain wave sensor, the computing system comprising:
an Alpha activity detection module configured to:
receive brain activity data of a user from a brain wave sensor, and
identify Alpha wave activity from the brain activity data;
a synchronization module configured to:
determine, based on the Alpha wave activity, a synchronization timing for presenting content to the user such that the content appears on a display device during a predetermined phase of the Alpha wave activity, the synchronization timing including a trigger point of the user's Alpha wave activity that indicates an onset of the predetermined phase,
determine a processing delay between triggering presentation of content and presenting the content on the display, wherein the synchronization timing accounts for the delay; and
a content presentation module configured to cause, in response to detecting the trigger point of the user's Alpha wave activity, the content to be displayed on the display device according to the synchronization timing, the content including a first content item and a second content item that is associated with the first content item.

11. The system of claim 10, wherein the predetermined phase of the Alpha wave activity is a low power portion of the Alpha wave activity.

12. The system of claim 10, wherein the content presentation module is further configured to:
receive, in response to displaying the content, a user input indicating an association made by the user based on the content displayed to the user; and
determine, based on the user input, whether the user has made a correct association based on the content displayed to the user.

13. The system of claim 12, wherein the content presentation module is further configured to present, to the user, an output that indicates whether the user made the correct association with the content.

14. A non-transient computer readable storage medium storing instructions that, when executed by at least one processor, cause the at least one processor to perform operations comprising:
receiving brain activity data of a user from a brain wave sensor;
identifying Alpha wave activity from the brain activity data;
determining, based on the Alpha wave activity, a synchronization timing for presenting content to the user such that the content appears on a display device during a predetermined phase of the Alpha wave activity, the synchronization timing including a trigger point of the user's Alpha wave activity that indicates an onset of the predetermined phase;
determining a processing delay between triggering presentation of content and presenting the content on the display, wherein the synchronization timing accounts for the delay; and
in response to detecting the trigger point of the user's Alpha wave activity, causing the content to be displayed on the display device according to the synchronization timing, the content including a first content item and a second content item that is associated with the first content item.

15. The medium of claim 14, wherein the predetermined phase of the Alpha wave activity is a low power portion of the Alpha wave activity.

16. The medium of claim 14, further comprising:
receiving, in response to displaying the content, a user input indicating an association made by the user based on the content displayed to the user; and
determining, based on the user input, whether the user has made a correct association based on the content displayed to the user.

17. The medium of claim 16, further comprising presenting, to the user, an output that indicates whether the user made the correct association with the content.

18. A computer-implemented method executed by one or more processors and comprising:
receiving brain activity data of a user from a brain wave sensor;
identifying Alpha wave activity from the brain activity data;
determining, based on the Alpha wave activity, a synchronization timing for presenting content to the user such that the content appears on a display device during a predetermined phase of the Alpha wave activity, wherein the predetermined phase of the Alpha wave activity is a low power portion of the Alpha wave activity; and
causing the content to be displayed on the display device according to the synchronization timing, the content including a first content item and a second content item that is associated with the first content item.

19. A system comprising:
a brain wave sensor; and
a computing system communicably coupled to the brain wave sensor, the computing system comprising:
an Alpha activity detection module configured to:
receive brain activity data of a user from a brain wave sensor, and identify Alpha wave activity from the brain activity data;
a synchronization module configured to determine, based on the Alpha wave activity, a synchronization timing for presenting content to the user such that the content appears on a display device during a predetermined phase of the Alpha wave activity, wherein the predetermined phase of the Alpha wave activity is a low power portion of the Alpha wave activity; and
a content presentation module configured to cause the content to be displayed on the display device according to the synchronization timing, the content including a first content item and a second content item that is associated with the first content item.

20. A non-transient computer readable storage medium storing instructions that, when executed by at least one processor, cause the at least one processor to perform operations comprising:
receiving brain activity data of a user from a brain wave sensor;
identifying Alpha wave activity from the brain activity data;
determining, based on the Alpha wave activity, a synchronization timing for presenting content to the user such that the content appears on a display device during a predetermined phase of the Alpha wave activity, wherein the predetermined phase of the Alpha wave activity is a low power portion of the Alpha wave activity; and
causing the content to be displayed on the display device according to the synchronization timing, the content including a first content item and a second content item that is associated with the first content item.

* * * * *